United States Patent [19]

Varwig

[11] Patent Number: 5,034,156

[45] Date of Patent: Jul. 23, 1991

[54] METHOD FOR INHIBITING THE POLYMERIZATION OF ACRYLIC ACID

[75] Inventor: John W. Varwig, Berkeley, Mo.

[73] Assignee: Mallinckrodt Specialty Chemicals Company, St. Louis, Mo.

[21] Appl. No.: 463,940

[22] Filed: Jan. 8, 1990

Related U.S. Application Data

[63] Continuation of Ser. No. 182,532, Apr. 18, 1988, abandoned.

[51] Int. Cl.$^5$ .......................... C08F 2/38; C09K 15/00
[52] U.S. Cl. .......................................... 252/403; 203/8; 252/404; 252/405; 562/598
[58] Field of Search ..................... 203/8; 252/403, 404, 252/405; 562/598

[56] References Cited

U.S. PATENT DOCUMENTS

| | | | |
|---|---|---|---|
| 2,758,131 | 8/1956 | Caivillon | 558/306 |
| 3,426,063 | 2/1969 | Joseph | 585/5 |
| 3,674,651 | 7/1972 | Otsuki et al. | 203/8 |
| 3,959,358 | 5/1976 | Gurish | 203/8 |
| 4,013,580 | 3/1977 | Hayashi et al. | 252/403 X |
| 4,016,216 | 4/1977 | Shimizu et al. | 252/403 X |
| 4,137,273 | 1/1979 | Siddall | 568/648 |
| 4,140,606 | 2/1979 | Sakimoto et al. | 522/22 |
| 4,188,222 | 2/1980 | Nezu et al. | 430/284 |
| 4,210,493 | 7/1980 | Stewart et al. | 203/8 |
| 4,258,123 | 3/1981 | Nagashima et al. | 84/1.26 |
| 4,310,676 | 1/1982 | Schropp | 560/4 |
| 4,317,926 | 2/1982 | Sato et al. | 203/8 |
| 4,338,162 | 5/1982 | Johnson | 203/8 |
| 4,466,905 | 8/1984 | Butler et al. | 252/403 X |
| 4,654,451 | 3/1987 | Miller et al. | 252/403 X |
| 4,666,993 | 5/1987 | Urano et al. | 525/328.2 |
| 4,769,485 | 9/1988 | Urano et al. | 560/340 |
| 4,788,256 | 11/1988 | Aoki et al. | 525/326.8 |
| 4,810,618 | 3/1989 | Koike et al. | 430/281 |
| 4,812,486 | 3/1989 | Hosokawa et al. | 424/418 X |

FOREIGN PATENT DOCUMENTS 63-126853  5/1988  Japan .

*Primary Examiner*—Deborah L. Kyle
*Assistant Examiner*—Valerie Fee
*Attorney, Agent, or Firm*—Grace L. Bonner

[57] ABSTRACT

A new and improved polymerization inhibitor composition, its method of manufacture, and its use in stabilizing the distillation of acrylic acid is made possible by the pre-oxygen-activation of N-nitrosophenylhydroxylamine in combination with hydroquinone mono-methylether (often referred to as p-methoxyphenol) whereupon a synergistic performance of these components is disclosed.

11 Claims, No Drawings

METHOD FOR INHIBITING THE POLYMERIZATION OF ACRYLIC ACID

This is a continuation of application Ser. No. 182,532, filed Apr. 18, 1988, now abandoned.

BACKGROUND OF THE INVENTION

1. FIELD OF THE INVENTION

The present invention relates to compositions for inhibiting the polymerization of acrylic acid, and methods of manufacturing the composition. This invention is particularly useful for preventing the polymerization of acrylic acid upon its distillation. Accordingly, the invention also relates to processes for stabilizing the distillation of acrylic acid.

2. DESCRIPTION OF THE PRIOR ART

Although acrylic acid was first prepared in 1847, and although its polymerization has been known for over a century, means for addressing the technical difficulties associated with its manufacture and polymerization have only begun to surface since 1930. These processes for manufacturing acrylic acid, and particularly its concentration and purification, have normally comprised various thermal distillation techniques. It is widely known that the principal losses of acrylic acid in these operations are due to thermal polymerization of the acrylic acid monomers. However, since the thermal energy is essential in these distillation operations, various devices or means for inhibiting the polymerization despite the presence of heat have been variously considered over the years. Notably, mild operating conditions, rapid through put avoiding residence time of the acrylic acid, and feeding polymerization inhibitors into the distillation device have been employed for this purpose.

In the past, a number of polymerization inhibitors have been tried, either singly or as combinations of two or more and often synergized by molecular oxygen bubbled through the distillation column during the course of aerobic distillations. Such inhibitors include para methoxy phenol (herein referred to as hydroquinone-mono-methyl-ether (MEHQ)), phenothiazine (PTZ), catechol, methylene-blue, diphenylamine, various organic copper salts, particular aromatic nitroso compounds and other phenolic, amine, nitro, and quinone compounds and their inorganic salts. However, for the most part, these polymerization inhibitors have been specific for vapor phase polymerization inhibition or alternatively liquid phase polymerization inhibition.

U.S. Pat. No. 3,674,651 discloses a polymerization inhibitor composition for acrylic acid comprising molecular oxygen, diphenylamine or its derivatives and either benzoquinone or MEHQ. However, the process for synergizing the composition calls for introducing the inhibitors at the top vapor phase of the column, while adding an additional general liquid phase polymerization inhibitor to the liquid phase and supplying air or oxygen up through the bottom of the column to effect the stabilization.

U.S. Pat. No. 4,021,310 discloses a polymerization inhibiting procedure for acrylic acid in vapor-phase catalytic oxidation requiring at least one inhibitor such as MEHQ or PTZ combined with particular carbamate or salicylate copper salts and air or molecular oxygen bubbled into the distillation column.

In 1976 Mr. Myron J. Jursich theorized in his U.S. Pat. No. 3,959,358 that phenol-type polymerization inhibiting compositions such as MEHQ (para methoxy phenol) for acrylate esters were made effective in the presence of dissolved oxygen if combined in an excess molar amount with various amine type inhibitors such as PTZ. He theorized that phenol-type inhibitors satisfactorily prevent thermally activated polymerization of acrylic esters when little or no oxygen is present. However, according to Jursich, when oxygen is present in the ester solution such as from polymerization initiating species like peroxides, the phenol-type inhibitor alone is inadequate. Accordingly, various amine-type inhibitors, particularly phenothiazine (PTZ), were used to scavenge the dissolved oxygen without air or oxygen bubbled into the column. However, unlike acrylic esters, this theory has been found to be ineffective with acrylic acid.

N-nitrosophenyl-hydroxylamine (NPH) has been known as a stabilizer inhibiting the polymerization of monomers for a number of years. See for example, U.S. Pat. No. 2,758,131 and German Pat. No. 1,180,733. Also, U.S. Pat. No. 3,426,063 discloses its use in inhibiting the polymerization of water soluble acrylate esters but not acrylic acid. In the past, the use of NPH as a polymerization inhibitor for acrylic acid has had a number of drawbacks including the need for using it in such higher concentration that the water of dissolutions has a deleterious effect on the distillation operation.

Mr. Thomas Stewart discloses in his U.S. Pat. No. 4,210,493 that in certain anaerobic conditions common to acrylic acid distillation such as vapor spaces, overheads, unvented reflux columns, and especially when vacuum distillation is involved, a lack of oxygen flowing through the equipment renders total loss of inhibitory properties to most known inhibitors when attempting to inhibit polymerization of acrylic acid. Certain aliphatic C-Nitroso compounds are said to overcome that problem for acrylic acid vapor phase polymerization inhibition where there is no air or oxygen present.

U.S. Pat. No. 4,310,676 discloses another polymerization inhibitor composition for acrylic acid under anaerobic sealed storage conditions comprising phenothiazine (PTZ) and paranitrosophenol.

A new and improved polymerization inhibiting composition for acrylic acid in both the vapor and liquid phases devoid of the prior art problems would be a substantial advancement in the art.

SUMMARY OF THE INVENTION

It is a principal object of the present invention to provide a novel, synergistic composition of matter for inhibiting the polymerization of acrylic acid.

It is a further important object to provide a composition of matter for inhibiting polymerization of acrylic acid which composition has exceptionally good performance in both the liquid and vapor phase during distillation.

It is still a further object to provide a novel method for making a synergistic polymerization inhibiting composition for acrylic acid.

It is a still further object of the present invention to provide a novel method for making a synergistic polymerization inhibitor for acrylic acid from components of the composition which are ordinarily ineffective when combined.

Another object of the present invention is to provide a novel method for improving the performance of NPH as a polymerization inhibitor for acrylic acid.

Still another objection of the present invention is to provide a novel method for improving the performance of MEHQ as a polymerization inhibitor for acrylic acid.

It is still a further principal object of the present invention to provide a method for stabilizing the distillation of acrylic acid without the need for bubbling air or molecular oxygen into the distillation equipment.

An additional object of the present invention is to provide a novel method for synergizing a polymerization inhibiting composition for acrylic acid without the need for bubbling air or oxygen during distillation preparation or purification of the acid.

Still other objects and advantages of the invention will be apparent to those skilled in the art upon reference to the following detailed description of the preferred embodiments and the appended examples.

DETAILED DESCRIPTION AND PREFERRED EMBODIMENTS

In accordance with the present invention, it has been discovered that thermal polymerization of acrylic acid in the liquid and/or vapor phases may be inhibited in an unusually effective manner by a novel composition of matter comprising pre-oxygen-activated N-nitrosophenolhydroxylamine (NPH) and para-methoxy-phenol herein referred to as hydroquinone mono-methyl-ether (MEHQ). The effective polymerization inhibition obtained from NPH and MEHQ when combined to produce the composition of the present invention is much greater than that obtained when either inhibitor is used alone or in combination with other commercially available inhibitors such as phenothiazine. Although the chemistry of the interaction of NPH and oxygen, and of NPH and MEHQ is not understood, we would like to offer one possible explanation for the phenomenon of the present invention. That is, we have discovered that NPH and MEHQ when combined ordinarily do not provide very good polymdrization inhibition. It may be possible that NPH reacts or interacts very rapidly with MEHQ to give a form or complex or reaction product which is ineffective. However, it may be possible that NPH is activated by, or interacts in some way with, or is oxidized by the dissolved oxygen in such acid solutions if thoroughly agitated and allowed to stand or sit during a short interval of time, for example 1 to 4 minutes often referred to by us as a residence time. This reaction or interaction of NPH with oxygen if occurring is slower than the interaction of NPH with MEHQ. Thus, so long as NPH is in substantial molar excess over any amount of MEHQ that may be present during the residence time, then a subsequent addition of MEHQ to provide a molar excess over that of the NPH results in an unusually effective polymerization inhibitor. Accordingly, although we do not know the exact chemical specie or species of NPH that is so effective of an inhibitor to the polymerization of acrylic acid upon combination with MEHQ, we have nevertheless described this component of the composition of the present invention as pre-oxygen-activated NPH.

Pre-oxygen-activated NPH is derived from aqueous solutions of NPH, preferably the ammonium salt which is often referred to as cupferron. Other water soluble salts of NPH which may be employed to prepare such aqueous solutions include for example, alkali metal salts such as sodium; amine salts such as ethylamine, and alkanolamine salts such as ethanolamine, or any salt of NPH which has a solubility of at least 5% in water, alcohol, ester, ether or other solvents compatible with acrylic acid, and which will not deleteriously effect the quality of acrylic acid. Any. convenient concentration of solution may be employed. It has been found to be particularly desirable and preferred that when using cupferron as a source of NPH, an aqueous solution of about 10% NPH is utilized. A sufficient molar amount of NPH to provide the requisite level or concentration of NPH desired in the final acrylic acid to be stabilized from thermal polymerization is added to a small amount of a weak acid such as acrylic acid or acetic, agitated, and permitted a residence time for pre-oxygen activation of the NPH. Preferably, the amount of NPH desired for the effective polymerization inhibitor composition ranges from 50 ppm to 150 ppm based upon the final weight of acrylic acid. Accordingly, it is preferred to, employ from 0.001 gram (1 gram/liter) to 0.006 gram (6 grams/liter) of NPH per ml of acrylic acid or preferably 2000 ppm during the pre-oxygen stage of this process and for the preparation of what we have referred to as pre-oxygen-activated NPH.

Acrylic acid is often commercially available after having been pre-stabilized with from about 100 to 200 ppm MEHQ. However, as we have previously indicated, such pre-stabilized acrylic acid with such levels of MEHQ either alone or in combination with other inhibitors such as PTZ, have an inferior performance to the composition of the present invention. Also, acrylic acid pre-stabilized with such concentrations of MEHQ are ordinarily rendered less effective upon the addition of NPH. Nevertheless, we have found that so long as NPH is in substantial excess to the amount of MEHQ in such acrylic acid and sufficient residence time is allowed after mixing the NPH into the solution, there can be formed the pre-oxygen-activated NPH of the invention. One preferred embodiment of the present invention calls for mixing a small amount of acrylic acid containing from 0 to 200 ppm MEHQ with a substantial molar excess of NPH ranging from 10 moles NPH/mole MEHQ to 50 moles NPH/mole MEHQ. It must be remembered however that pre-oxygen activation can occur in the total absence of MEHQ and it can occur when the NPH is added to a weak acid other than acrylic acid, as for example, acetic acid.

Following the preparation of pre-oxygen activated NPH, MEHQ is added. Preferably, MEHQ is dissolved in the acrylic acid at a stabilizing amount and the MEHQ solution is added to the pre-oxygen activated NPH to provide a composition having from 50 to 150 ppm NPH based upon the weight of the acrylic acid and from 200 to 400 ppm of the MEHQ based upon the weight of the acrylic acid.

The inhibitor composition of the present invention may be employed to inhibit polymerization during the preparation of acrylic acid as well as during the purification of these monomers by distillation. The inhibitor composition may be either pre-prepared or may be contacted with crude impure monomer and formed in situ in the kettle of the distillation system prior to distillation as is the preferred method. The mixture of acrylic acid and the inhibitor composition of the present invention ma be distilled under substantially anaerobic conditions and condensed outside of the distillation zone. The inhibitors may also be added to the plates of the distillation column during distillation to prevent polymer formation therein. Additionally, purified monomers are effectively stabilized against polymerization during storage under anaerobic conditions and above 15° C.

temperature by the addition of the inhibitors of this invention.

Although the composition of the present invention provides a synergistic polymerization inhibition, without the need for bubbling oxygen through the distillation column, and although substantial residence time during acrylic acid distillation as that needed to bring about pre-oxygen-activated NPH is ordinarily avoided, it may be possible to pre-oxygen activate solutions of NPH and acrylic acid in the column prior to the addition of substantial molar excesses of MEHQ if sufficiently long distillation columns were designed to accomplish the objective of the present invention.

As above noted, the desired concentrations of the NPH and MEHQ give rise to preferred weight ratios of pre-oxygen activated NPH to MEHQ ranging from 0.125 to about 0.75. Preferably, a ratio of from 0.4 to 0.6 is desired.

The ordinary distillation of acrylic acid involves vacuum distillation under pressures of from about 50 mm Hg to 150 mm Hg and temperatures ranging from about 90° C. to 120° C. The composition of the present invention serves to stabilize such distillations in an unusually effective manner. Additionally, the invention may have utility in the preparation of acrylic acid during catalytic oxidation procedures.

The novel polymerization inhibiting compositions of the present invention show unusual effects in both the liquid and vapor phases of acrylic acid distillation. The induction period for the onslaught of polymerization by the development of haze in the liquid is measured in ascertaining the effectiveness of the polymerization composition. The effectiveness of the polymerization inhibition of the vapor phase is measured in the traditional manner of positive or negative weight gain with regard to a popcorn polymer bead placed at the top of the distillation.

The following examples are given for more specifically illustrating the invention.

THE EXAMPLES

In the examples, a round bottom flask equipped with a Vigreux column (30 cm long) and a vacuum source was employed to measure the effectiveness of the inhibitors tested. The flask was heated by an oil bath and agitation was provided by means of a magnetic stirring device. A small stainless steel mesh basket containing an accurately weighed kernel of styrene-butadiene rubber popcorn (0.01 –0.02 gms) was affixed to the top of the column in order that the kernel could be suspended in the vapor phase region of the flask well above the liquid phase during heating of the contents of the flask.

In each test 100 ml of glacial acrylic acid containing the inhibitor or inhibitors to be tested was added to the flask. The acrylic acid was stirred and heated under reduced pressure to provide refluxing well up into the Vigreux column. The refluxing took place anaerobically at a pressure of between 50 and 60 mm of mercury and the temperature employed was from 95 to 105° C. The refluxing was continued for 6 hours, or less if polymerization was observed to be occurring rapidly.

Both vapor phase polymerization inhibition and liquid phase polymerization inhibition were measured. At the end of the refluxing time interval, the popcorn kernel was recovered, dried and weighed. The percent change in weight of the kernel was calculated. No increase in its weight or a negative weight change indicated complete inhibition of vapor phase polymerization. An increase in weight indicated the relative degree of positive vapor phase polymerization. Liquid phase polymerization inhibition was measured by the amount of time required for the liquid phase to become hazy which haze indicates the presence of polymer in the liquid.

The specific examples are listed below and their results are tabulated in Table 1. All concentrations are by weight, N-nitrosophenylhydroxylamine has been abbreviated to NPH, and hydroquinone-mono-methyl-ether has been abbreviated to MEHQ. The NPH is used in the form of its ammonium salt.

EXAMPLE 1

To 6 ml of acrylic acid stabilized with 200 ppm of MEHQ was added 0.013 gms of NPH, as a 10% water solution, creating a substantial molar excess of NPH. The solution was stirred and allowed to stand for between 3 and 4 minutes. Then, 94 ml of the acrylic acid stabilized with 200 ppm of MEHQ was added to the flask of the test apparatus and combined with the 6 ml aliquot described above to provide 100 ml of solution containing 124 ppm of NPH and 200 ppm of MEHQ. The solution was refluxed for 6 hours and resulted in excellent polymerization inhibition as reflected in Table 1. The stirring of the 6 ml aliquot of acrylic acid containing the substantial molar excess of NPH under ambient conditions allowed air equilibration of the mixture and the 3 to 4 minute residence time was sufficient to oxygen-activate the NPH in situ from dissolved oxygen. This in turn permitted synergistic polymerization inhibition when MEHQ was added in molar excess.

EXAMPLE 2

The same procedure as Example 1 was followed except that 0.0115 gms of NPH was added to a 5 ml aliquot of the acrylic acid, and the solution was allowed to stand for 4 minutes prior to combining the aliquot with 95 ml of the acrylic acid. The concentration of NPH finally tested was 110 ppm. Like that of Example 1, exceptional polymerization inhibition was observed.

EXAMPLE 3

A similar procedure of Examples 1 and 2 was followed except that the acrylic acid stabilized with 200 ppm MEHQ was first distilled to give essentially inhibitor-free acrylic acid. To 20 ml of the inhibitor-free acrylic acid was added 0.013 gms of NPH as a 10% water solution and mixed. To 80 ml of this distilled inhibitor-free acrylic acid was added 0.0227 gms of MEHQ and mixed. After one minute, the two solutions were combined in the test flask and tested for vapor and liquid phase polymerization inhibition. The concentration of MEHQ was 216 ppm and the concentration of NPH was 124 ppm. The results were again exceptional polymerization inhibition and the NPH was oxygen activated without any need for even a small percentage of MEHQ during the air equilibration interval.

EXAMPLE 4

A similar procedure to the previous examples was followed except that the NPH was oxygen activated in acetic acid. To 4.5 ml of acetic acid in a vial was added 0.003 gms of NPH, as a 3% aqueous solution (0.1 ml), and the solution was mixed and allowed to stand for one minute. This solution was then added to 100 ml of acrylic acid which contained 200 ppm MEHQ, and this solution was added to the flask of the test apparatus and the solution was tested for polymerization inhibition. The solution tested contained 29 ppm of NPH by weight of the acrylic acid and 200 ppm of MEHQ by weight of the acrylic acid. Again, polymerization inhibition was achieved in both the liquid and vapor phases.

EXAMPLE 5

The same procedure of Example 4 was followed except that to 4 ml of acetic acid was added 0.0018 gms of NPH as a 1.8% aqueous solution. After about one minute that solution was combined with the 100 ml of acrylic acid containing 200 ppm of MEHQ and the combination tested. The composition comprised 17 ppm of NPH and of course 200 ppm of MEHQ both based on the weight of acrylic acid. Again, excellent results were obtained where the oxygen-activation of NPH took place in acetic acid.

EXAMPLE 6

A similar procedure to the previous examples was followed except that the initial aliquot of NPH was protected from air and thus not allowed to combine with oxygen for activation. The acrylic acid used contained 200 ppm MEHQ. However, 6 ml of that acrylic acid were sparged with nitrogen for several minutes to remove the dissolved oxygen. Then, a nitrogen blanket was kept over the solution and 0.013 gms of NPH was added, as a 10% water solution, and mixed. While maintaining the nitrogen blanket, the NPH solution in acrylic acid was allowed to stand for 4 minutes. Then the solution was combined with 94 ml of the acrylic acid containing 200 ppm of MEHQ, again while under the nitrogen blanket. The combination was added to the distilling flask and the polymerizatio inhibition tested. The level NPH was 124 ppm and the level of MEHQ was 200 ppm. Very poor polymerization inhibition resulted in both the liquid and vapor phases. This test demonstrates that absent oxygen activation, the NPH combined with MEHQ is a poor polymerization inhibition composition for acrylic acid.

EXAMPLE 7

This example differed from the procedures of the previous examples in that oxygen activation of NPH was attempted while MEHQ was present in a molar excess. To a 5 ml vial of acrylic acid containing 200 ppm MEHQ was added an additional 0.0253 gms of MEHQ. To this 5 ml solution was added 0.0123 gms of NPH as a 10% water solution. The mole ratio of MEHQ to NPH in this 5 ml solution was 2.7:1.0. The solution was allowed to stand for 6 minutes and then combined with 95 ml of acrylic acid containing 200 ppm MEHQ such that the 100 ml solution contained 117 ppm of NPH and 440 ppm of MEHQ and this solution was tested for polymerization inhibition. Very poor results were achieved demonstrating that NPH even though exposed to dissolved oxygen, will not activate when MEHQ is present in excess. Apparently, in acrylic acid or for that matter, other acids such as acetic acids, NPH reacts or interacts very rapidly with MEHQ to give a form, complex or reaction product of these two inhibitors which does not provide very good polymerization inhibition. See Table 1.

EXAMPLE 8

In a similar manner to Example 7, an excess of MEHQ was combined with NPH except that no time was allowed for the NPH mixture to stand. That is, to 0.013 gms of NPH in a flask was added 100 ml of acrylic acid containing 200 ppm MEHQ. The concentration of NPH was thus 124 ppm as compared to the 200 ppm of MEHQ. The solution was mixed and immediately transferred to the test apparatus and tested for polymerization inhibition. Again, poor results were achieved and it was demonstrated that the interaction or reaction between MEHQ and NPH occurs very rapidly rendering ineffectiveness and/or an inability of the NPH to oxygen activate. This particular excess of MEHQ was not as large as that from Example 7.

EXAMPLE 9

A similar procedure as that of Example 8 was conducted except that the NPH was in a substantial molar excess over that of the MEHQ. That is, to 100 ml of acrylic acid which contained 200 ppm of MEHQ, was added while stirring 0.065 gms of NPH as a 10% water solution giving 619 ppm of NPH. The results were not very good demonstrating that the residence time is essential for activating NPH and that NPH alone without such oxygen activation is not a very good polymerization inhibitor for acrylic acid.

EXAMPLE 10

This procedure was conducted to determine the effectiveness of MEHQ as a polymerization inhibitor of acrylic acid by itself anaerobically. That is, 0.021 gms of MEHQ was added to 100 ml of acrylic acid which already contained 200 ppm of MEHQ. The solution was therefore, brought up to a concentration of 400 ppm of MEHQ and was tested for inhibition effectiveness. The results show that MEHQ was a significantly poorer inhibitor than the composition of the present invention.

EXAMPLE 11

This example was conducted to determine whether oxygen-activated NPH alone is effective in inhibiting the polymerization of acrylic acid. To 20 ml of distilled acrylic acid containing no other inhibitor was added 0.013 gms of NPH as a 10% water solution. The solution was mixed with aerobically and allowed to stand for about one minute. Then, 80 additional ml of the distilled acrylic acid was added bringing the concentration of NPH to 124 ppm. The 100 ml was added to the test apparatus and tested for polymerization inhibition. However, the acrylic acid polymerized so rapidly that the basket containing the popcorn kernel was blown off of its support, and could not be recovered from the polymerized acrylic acid liquid. This demonstrates that even oxygen activated, the NPH alone was not an effective polymerization inhibitor, but rather it may have even promoted the violent polymerization after 50 minutes of reflux.

EXAMPLE 12

This example was conducted to test the premise of U.S. Pat. No. 3,959,358, which theorized that certain phenyl-type inhibitors such as MEHQ which are ineffective inhibitors of acrylic esters when oxygen is present can be made effective by adding certain amine-type inhibitors such as phenothiazine which are oxygen scavengers. So long as the MEHQ is in excess of the phenothiazine (PTZ) effective polymerization inhibition is expected. However, in this example, acrylic acid containing 200 ppm of MEHQ was treated with PTZ prepared in the same manner as was effective for NPH. That is, 6 ml of the acrylic acid were added to 0.0132 gms of PTZ and mixed while the PTZ was in a substantial molar excess. After standing several minutes, the 6 ml solution was combined with 94 ml of acrylic acid bringing the concentration of PTZ to 126 ppm while having the MEHQ at 200 ppm. The polymerization inhibition as can be seen from Table 1 was very poor and quite inferior to the composition of the present invention.

TABLE 1

| EXAMPLE NO. | MEHQ Level, ppm | NPH Level, ppm | % Weight Change in Popcorn Seed | Time of Reflux | Time Liquid Phase Remained Clear |
|---|---|---|---|---|---|
| 1 | 200 | 124 | −2.4 | 6 hrs | 6 hrs. |
| 2 | 200 | 110 | −7.8 | 6 hrs. | 6 hrs. |
| 3 | 216 | 124 | −1.2 | 6 hrs. | 6 hrs. |
| 4 | 200 | 29 | −0.7 | 6 hrs. | 6 hrs. |
| 5 | 200 | 17 | +2.7 | 6 hrs. | 6 hrs. |
| 6 | 200 | 124 | 639. | 4 hrs. | 1 hr. |
| 7 | 440 | 117 | 592. | 5 hrs. | 40 min. |
| 8 | 200 | 124 | 644. | 5 hrs. | 30 min. |
| 9 | 200 | 619 | 252. | 70 min. | 45 min. |
| 10 | 400 | — | 277. | 35 min. | 15 min. |
| 11 | — | 124 | —[a] | 50 min. | 20 min. |
| 12 | 200 | —[b] | 636 | 6 hrs. | 36 min. |

[a] Polymerized violently at 50 minutes reflux.
[b] No NPH used but contained 126 ppm PTZ.

What is claimed is:

1. A composition of matter for inhibiting the polymerization of acrylic acid during distillation and storage comprising
   (a) pre-oxygen-activated N-nitrosophenylhydroxylamine; and
   (b) hydroquinone-mono-methyl-ether in molar excess to said pre-oxygen-activated N-nitrosophenylhydroxylamine.

2. The composition of claim 1 having a relative weight ratio of pre-oxygen-activated N-nitrosophenylhydroxylamine to hydroquinone-mono-methyl-ether of from about 0.02 to 0.95, based on the weight of N-nitrosophenylhydroxylamine present 3. The composition of claim 1 or 2 concentrated in acrylic acid wherein the amount of (a) is from about 15 to about 125 ppm and the amount of (b) is from about 100 to about 450 ppm by weight of the acrylic acid.

4. A method for making an improved polymerization inhibitor for acrylic acid comprising (a) adding an effective amount of N-nitrosophenylhydroxylamine to a solution of an acid so that there is a molar excess of N-nitrosophenylhydroxylamine over any hydroquinone-mono-methyl-ether which may be present, under conditions such that the N-nitrosophenylhydroxylamine is oxygen activated;
   (b) thereafter, adding an amount of hydroquinone-mono-methyl-ether to provide a molar excess over the pre-oxygen-activated N-nitrosophenylhydroxylamine.

5. The method of claim 4 wherein the oxygen-activation occurs in situ by concentrating N-nitrosophenylhydroxylamine in air equilibrated acid at about 2,000 ppm for about 1 to 4 minutes.

6. The method of claim 4 wherein the amount of hydroquinone-mono-methyl-ether is added as an acrylic acid solution diluting the amount of pre-oxygen-activated N-nitrosophenylhydroxylamine to a concentration of from about 15 to about 125 ppm by weight based upon the acrylic acid and bringing the concentration of hydroquinone-mono-methyl-ether to about 100 to about 450 ppm by weight based upon the acrylic acid.

7. A process for stabilizing the polymerization of acrylic acid which comprises treating said acid with the combination of
   (a) pre-oxygen-activated N-nitrosophenylhydroxylamine; and
   (b) hydroquinone-mono-methyl-ether.

8. The process of claim 7 wherein the hydroquinone-mono-methyl-ether is in molar excess relative to the amount of pre-oxygen activated N-nitrosophenylhydroxylamine.

9. The process of claim 7 wherein the concentration of (a) is from 10 to 400 ppm by weight of the acrylic acid, and the concentration of (b) is from 100 to 500 ppm by weight of the carylic acid.

10. The process of claim 7 wherein the weight ratio of (a) to (b) is from about 0.95 to about 0.02.

11. The process of claim 7 wherein (a) is oxygen-activated by mixing air-equilibrated acrylic acid and N-nitrosophenylhydroxylamine in substantial molar excess of any hydroquinon-mono-ethyl-ether which may be present and allowing an effective residence time prior to combining substantial additional amounts of hydroquinone-mono-methyl-ether.

* * * * *

UNITED STATES PATENT AND TRADEMARK OFFICE
CERTIFICATE OF CORRECTION

PATENT NO. : 5,034,156
DATED : July 23, 1991
INVENTOR(S) : Varwig

It is certified that error appears in the above-identified patent and that said Letters Patent is hereby corrected as shown below:

Column 3, line 38, "polymdrization" should be --polymerization--

Column 4, line 2, delete the "." between "Any" and "convenient"

Column 4, line 16, delete the "," between "to" and "employ"

Column 8, line 60, "esters" should be --esters--

Signed and Sealed this

Second Day of February, 1993

Attest:

STEPHEN G. KUNIN

*Attesting Officer*      *Acting Commissioner of Patents and Trademarks*